(12) United States Patent
Gueret

(10) Patent No.: US 7,419,677 B2
(45) Date of Patent: *Sep. 2, 2008

(54) TREATMENT DEVICE AND METHOD OF USING THE SAME

(75) Inventor: Jean-Louis H. Gueret, Paris (FR)

(73) Assignee: L'Oreal S.A., Paris (FR)

( * ) Notice: Subject to any disclaimer, the term of this patent is extended or adjusted under 35 U.S.C. 154(b) by 66 days.

This patent is subject to a terminal disclaimer.

(21) Appl. No.: 10/107,410

(22) Filed: Mar. 28, 2002

(65) Prior Publication Data

US 2002/0142027 A1 Oct. 3, 2002

(30) Foreign Application Priority Data

Mar. 28, 2001 (FR) .................................. 01 04169

(51) Int. Cl.
*A61K 9/00* (2006.01)

(52) U.S. Cl. .................. 424/400; 424/402; 424/443; 604/292

(58) Field of Classification Search .................. 424/402, 424/404, 405, 443, 449; 604/292, 304; 128/857, 128/866, 879
See application file for complete search history.

(56) References Cited

U.S. PATENT DOCUMENTS

| | | | |
|---|---|---|---|
| 1,968,475 | A | 7/1934 | Beckwith et al. |
| 3,384,083 | A | 5/1968 | Cozza et al. |
| 3,428,043 | A | 2/1969 | Shepherd |
| 3,499,446 | A | 3/1970 | Tsuneizumi et al. |
| 4,122,554 | A | 10/1978 | Stager |
| 4,156,067 | A | 5/1979 | Gould |
| 4,337,859 | A | 7/1982 | Murphy et al. |
| 4,377,160 | A | 3/1983 | Romaine |
| 4,464,535 | A | 8/1984 | Szantay et al. |

(Continued)

FOREIGN PATENT DOCUMENTS

AT 353928 5/1979

(Continued)

OTHER PUBLICATIONS

Co-pending U.S. Appl. No. 09/779,095 Title: A Composite Structure Having an Adhesive Matrix Containing One or More Active Agents Invetor(s): Jean-Louis H. Gueret U.S. Filing Date: Feb. 8, 2001.

(Continued)

*Primary Examiner*—Michael G. Hartley
*Assistant Examiner*—Eric E. Silverman
(74) *Attorney, Agent, or Firm*—Finnegan, Henderson, Farabow, Garrett & Dunner, L.L.P.

(57) ABSTRACT

A treatment device may comprise a cover defining a cavity, wherein the cavity is configured to receive a part of a body. The cover may comprise at least one sheet having a composite structure. The composite structure may comprise at least two layers and at least one adhesive matrix situated between the two layers. At least one of the two layers may be permeable to a solvent, and the two layers may be permanently bonded to the adhesive matrix. The adhesive matrix may contain at least one active agent that is soluble in the solvent. When the active agent is dissolved in the solvent, the active agent may be released from at least one side of the cover.

63 Claims, 2 Drawing Sheets

U.S. PATENT DOCUMENTS

| | | |
|---|---|---|
| 4,548,861 A | 10/1985 | Barnes et al. |
| 4,585,797 A | 4/1986 | Cioca |
| 4,631,227 A | 12/1986 | Nakamura |
| 4,643,939 A | 2/1987 | Sugiyama et al. |
| 4,724,138 A | 2/1988 | Duffy et al. |
| 4,781,924 A | 11/1988 | Lee et al. |
| 4,804,538 A | 2/1989 | Chen |
| 4,814,167 A | 3/1989 | Wirth et al. |
| 5,026,552 A | 6/1991 | Gueret et al. |
| 5,049,376 A | 9/1991 | Murphy et al. |
| 5,078,160 A | 1/1992 | Carbonnier |
| 5,100,672 A | 3/1992 | Gueret et al. |
| 5,132,115 A | 7/1992 | Wolter et al. |
| 5,176,915 A | 1/1993 | Hoffmann |
| 5,176,917 A | 1/1993 | Müller |
| 5,232,707 A | 8/1993 | Lokensgard |
| 5,374,429 A | 12/1994 | Kinoshita et al. |
| 5,466,456 A | 11/1995 | Glover |
| 5,466,724 A | 11/1995 | Volke et al. |
| 5,505,956 A | 4/1996 | Kim et al. |
| 5,512,277 A | 4/1996 | Uemura et al. |
| 5,585,111 A | 12/1996 | Peterson |
| 5,653,970 A | 8/1997 | Vermeer |
| 5,702,713 A | 12/1997 | Joulia |
| 5,798,110 A | 8/1998 | Joulia |
| 5,800,835 A | 9/1998 | Zastrow et al. |
| 5,811,107 A | 9/1998 | Gangadharan et al. |
| 5,861,165 A | 1/1999 | Joulia |
| 5,935,596 A | 8/1999 | Crotty et al. |
| 5,958,443 A | 9/1999 | Viegas et al. |
| 5,961,988 A | 10/1999 | Zastrow et al. |
| 5,962,417 A | 10/1999 | Gilchrest et al. |
| 5,965,276 A * | 10/1999 | Shlenker et al. ............. 428/492 |
| 5,968,533 A | 10/1999 | Porter et al. |
| 5,972,360 A | 10/1999 | Braun |
| 6,063,398 A | 5/2000 | Gueret |
| 6,096,333 A | 8/2000 | Rolf et al. |
| 6,338,839 B1 | 1/2002 | Auguste et al. |
| 6,419,935 B1 | 7/2002 | Gueret |
| 6,623,751 B2 | 9/2003 | Gueret |
| 6,723,306 B2 | 4/2004 | Gueret |
| 6,730,317 B2 | 5/2004 | Gueret |
| 6,761,896 B1 | 7/2004 | Znaiden et al. |

FOREIGN PATENT DOCUMENTS

| | | |
|---|---|---|
| EP | 0 190 814 | 8/1986 |
| EP | 0 191 198 | 8/1986 |
| EP | 0 651 984 | 5/1995 |
| EP | 0 933 077 B1 | 8/1999 |
| EP | 0 953 460 A2 | 11/1999 |
| EP | 0 976 382 A1 | 2/2000 |
| EP | 0 976 383 | 2/2000 |
| EP | 0 998 903 A1 | 5/2000 |
| FR | 2 784 581 | 4/2000 |
| GB | 2 265 086 | 9/1993 |
| GB | 2 307 862 | 6/1997 |
| GB | 2 307 862 A | 6/1997 |
| JP | 54-132427 | 9/1979 |
| JP | 60-55955 | 4/1985 |
| JP | S62-177739 | 8/1987 |
| JP | 63-102718 | 7/1988 |
| JP | 10-167928 | 6/1998 |
| JP | 10-245319 | 9/1998 |
| JP | A 11-137338 | 5/1999 |
| WO | WO 87/05206 | 9/1987 |
| WO | WO 90/11065 | 10/1990 |
| WO | WO 94/02674 | 2/1994 |
| WO | WO 94/17837 | 8/1994 |
| WO | WO 94/22423 | 10/1994 |
| WO | WO 95/05204 | 2/1995 |
| WO | WO 95/28136 | 10/1995 |
| WO | WO 96/14822 | 5/1996 |
| WO | WO 96/37283 | 11/1996 |
| WO | WO 98/18441 | 5/1998 |
| WO | WO 98/31315 | 7/1998 |
| WO | WO 98/42303 | 10/1998 |
| WO | WO 99/13861 | 3/1999 |
| WO | WO 99/21532 | 5/1999 |
| WO | WO 00/16752 | 3/2000 |
| WO | WO 01/08658 | 2/2001 |
| WO | WO 01/10567 | 2/2001 |

OTHER PUBLICATIONS

English language Derwent Abstract of FR 2 784 581, Apr. 21, 2000.
Non-final Office Action dated May 19, 2004 (U.S. Appl. No. 09/779,095).
Supplemental Amendment dated Feb. 12, 2004 (U.S. Appl. No. 09/779,095).
Reply to Office Action dated Dec. 24, 2003 (U.S. Appl. No. 09/779,095).
Final Office Action dated Sep. 24, 2003 (U.S. Appl. No. 09/779,095).
Request for Reconsideration dated Jun. 26, 2003 (U.S. Appl. No. 09/779,095).
Non-final Office Action dated Feb. 26, 2003 (U.S. Appl. No. 09/779,095).
Request for Continued Examination dated Dec. 3, 2002 (U.S. Appl. No. 09/779,095).
Advisory Action dated Nov. 13, 2002 (U.S. Appl. No. 09/779,095).
Amendment dated Oct. 21, 2002 (U.S. Appl. No. 09/779,095).
Final Office Action dated Jul. 3, 2002 (U.S. Appl. No. 09/779,095).
Amendment dated Apr. 15, 2002 (U.S. Appl. No. 09/779,095).
Non-final Office Action dated Jan. 15, 2002 (U.S. Appl. No. 09/779,095).
Minolta brochure, "Precise Color Communication", 1994.
Minolta brochure, "Spectrophotometer CM-2002", 1991.
English language Derwent Abstract of FR 2 750 050.
English language Derwent Abstract of JP 61-112602.
English language Derwent translation of JP 10-167928.
English language Derwent Abstract of JP 10-324614.
English language Derwent translation of JP 10-245319.
English language translation of JP 10-287587.
Reply to Office Action dated Apr. 29, 2005, corresponding to U.S. Appl. No. 09/779,095.
Final Office Action dated Dec. 29, 2004, corresponding to U.S. Appl. No. 09/779,095.
Response to Office Action Under 37 C.F.R. § 1.111 dated Aug. 18, 2004, corresponding to U.S. Appl. No. 09/779,095.
U.S. Appl. No. 11/060,811; Title: Patch With a Magnetic Field Effect, Inventor: Jean-Louis H. Gueret, U.S. Filing Date: Feb. 18, 2005.

* cited by examiner

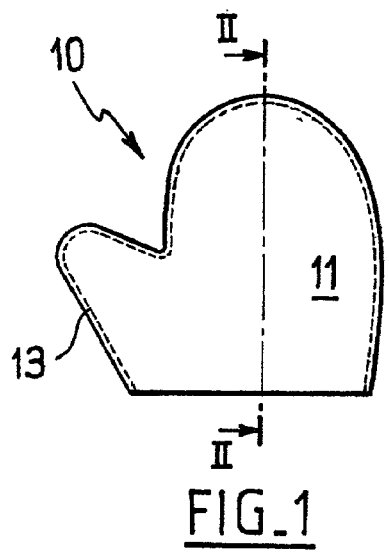
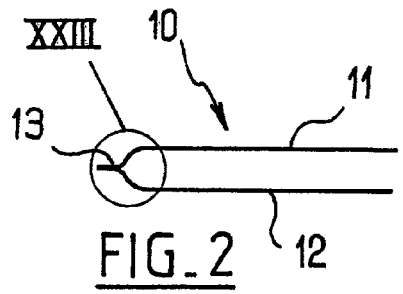
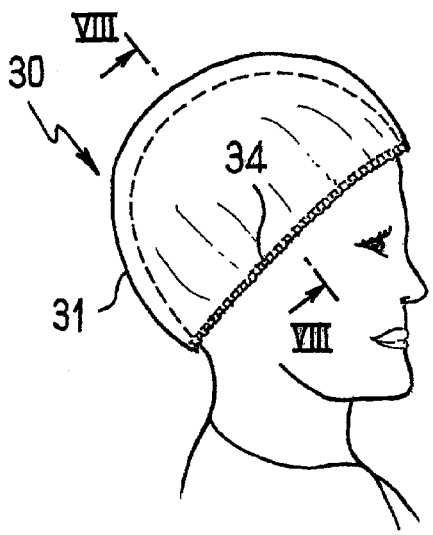
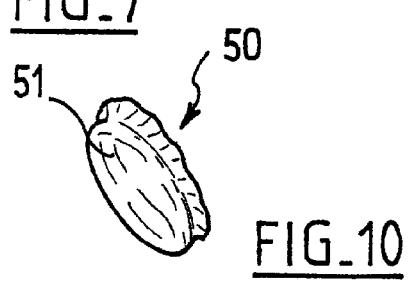
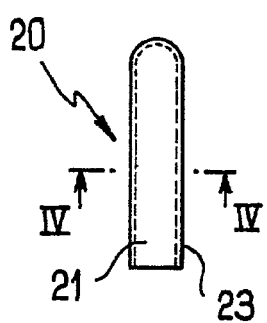
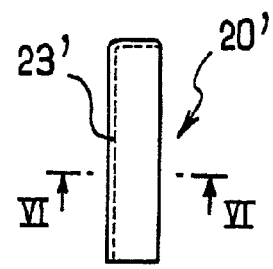
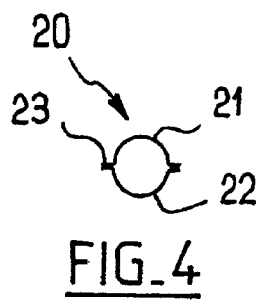
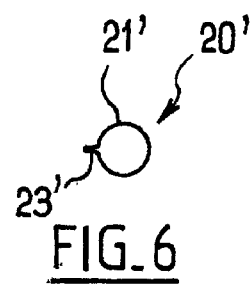
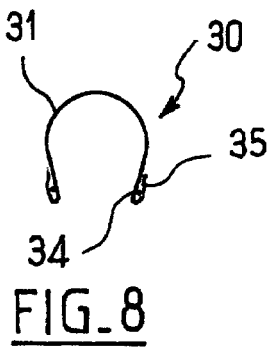
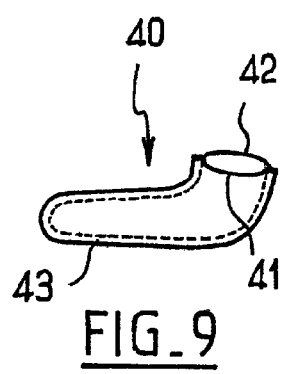
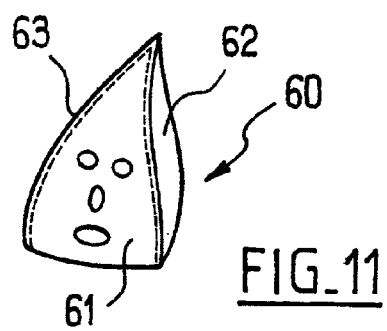

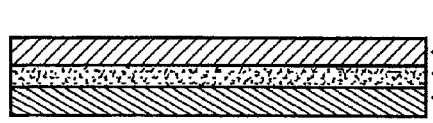
FIG_12
FIG_13
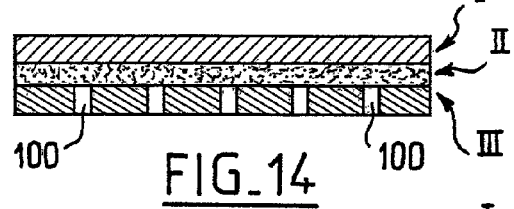
FIG_14
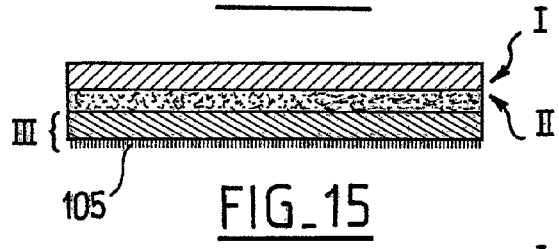
FIG_15
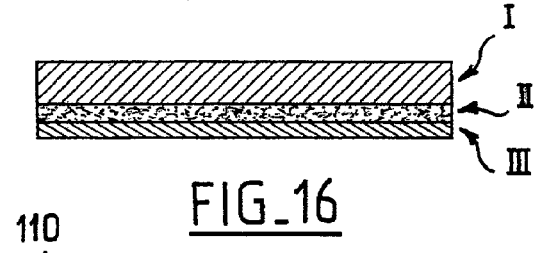
FIG_16
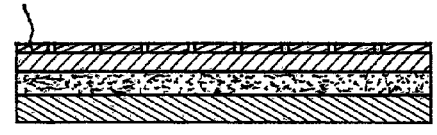
FIG_17
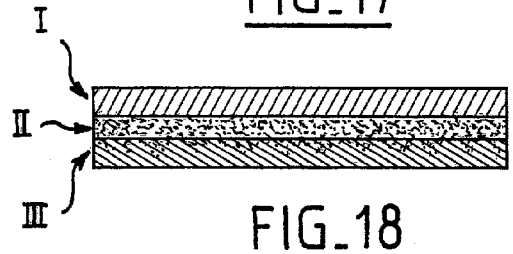
FIG_18
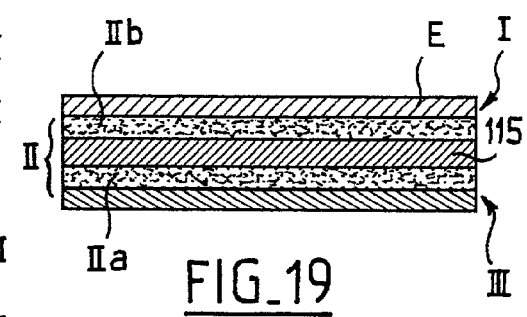
FIG_19
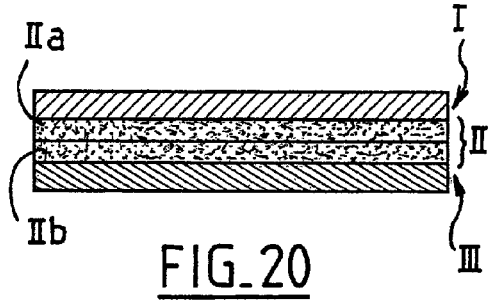
FIG_20
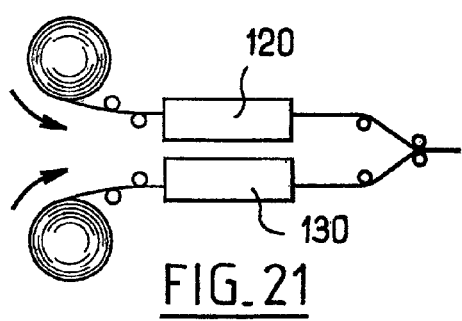
FIG_21
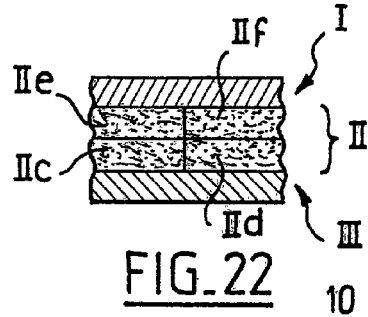
FIG_22
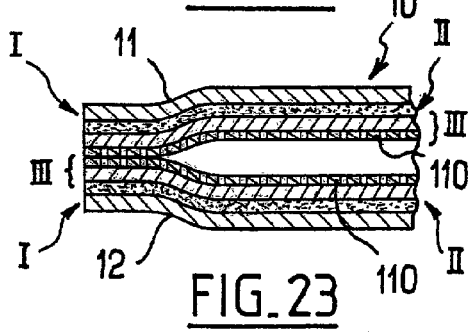
FIG_23

TREATMENT DEVICE AND METHOD OF USING THE SAME

The present invention relates to a device for treating a region of the human body, for example, the hands, the face, or the hair.

It may be beneficial to provide a treatment device which is easy to use, agreeable, and relatively simple to manufacture.

An exemplary treatment device in accordance with the invention may comprise a cover defining a cavity configured to receive a part of the body. The cover may comprise at least one sheet having a composite structure comprising at least one adhesive matrix situated between at least two layers, wherein at least one of the two layers may be permeable to a solvent. The two layers may be permanently bonded, directly or indirectly, to the adhesive matrix. The adhesive matrix may contain at least one active agent that is soluble in the solvent. The active agent, once dissolved, may be suitable for release from at least one side of the cover.

As used herein, two or more structural elements that are "permanently bonded" to each other cannot be readily separated from one another through the use of a completely manually-applied pulling force. For example, a release layer in contact with an adhesive on a bandage would not be "permanently bonded" to the remainder of the bandage.

An exemplary treatment device may easily perform treatment once all or part of the cover has been put into contact with the solvent, for example water. The treatment can take place inside the cover, outside the cover, or both inside and outside.

When the treatment takes place inside the cover, the active agent may be released on contact with the part of the body placed inside the cover, for example, a hand. The cover can facilitate the action of one or more active agents released on contact with the treated region, reinforcing the effectiveness of the treatment and, where appropriate, adding a thermal effect suitable for improving penetration of the one or more active agents into the skin.

When the treatment takes place outside the cover, the treatment device may be used like a face cloth, for example. A massaging action may be combined with an action of applying one or more active agents and/or with an action of cleaning the skin.

The cover may be in the form of a glove, for example, a mitten, so as to enable a hand to be treated and/or so as to enable the cover to be used to treat some other part of the body.

The cover may alternatively be in the form of a cap for placing over the head of a user for treating the hair or the scalp.

Alternatively, the cover may be in the form of a finger glove so as to enable a finger to be treated.

It should be appreciated that the cover may have various other forms. For example, the cover may be formed as a hood configured to treat the hair and/or the face, a sock, or a bag for placing around an ear, for example.

The cover may be elasticized, for example, around an opening where the inside of the cover communicates with the outside. The elasticized opening may hold the cover better on the part of the body that is received inside. The elasticized opening may allow the cover to form a bag.

The cover may be made out of a single sheet that is folded over onto itself or shaped to form a bag. Alternatively, the cover may be made from two or more sheets that are assembled together.

When two sheets are assembled together, assembly may be performed over a portion of the periphery of the sheets, so as to leave an opening for inserting a part of the body.

The sheets may be assembled together by, for example, heat-sealing, adhesive, or stitching.

The cover may have slots or openings disposed in a staggered configuration as in expanded metal, so as to be extensible to some extent.

According to an exemplary embodiment, the adhesive matrix may contain one or more active agents that are soluble in the solvent used and/or capable of swelling on coming into contact with the solvent. The agents may be introduced into the matrix in sufficient quantity for the matrix to lose its cohesion on contact with the solvent so as to release one or more of the active agents more easily. Alternatively or additionally, the adhesive matrix may contain a filler of one or more compounds capable of swelling on contact with the solvent. The filler may be introduced into the matrix in sufficient quantity for it to lose its cohesion on coming into contact with the solvent and for it to release one or more of the active agents more easily. Alternatively or additionally, the adhesive matrix may contain a filler of one or more substantially inert compounds in sufficient quantity for the matrix to lose its cohesion on contact with the solvent and thus release one or more of the active agents more easily.

The adhesive matrix may comprise one or more moisture-absorbing compounds, for example, 0.2% to 60% by weight of a moisture-absorbing compound, or 0.5% to 40% by weight of a moisture-absorbing compound. The compound may be selected from polyacrylates, silicas, cotton fibers, starches, alginates, calcium and magnesium carbonates, viscose, cellulose, lyophylisates, and the like. In addition to (or in the alternative to) moisture-absorbing compounds, the adhesive matrix may include one or more substances capable of reducing its adhesive power and enabling it to burst on contact with the solvent so as to facilitate release one or more of the active agents. The substances may comprise, for example, substantially inert substances such as microbeads or a powder of an inert compound, for example, the polyamide powder known by the name ORGASOL.

The adhesive matrix may include one or more active agents selected from vitamin C, vitamin A, vitamin F, glycerin, laponite, wetting agents, collagen, salicylic acid, tio acid, essential aromatic oils, coloring agents, caffeine, anti-oxidants, free radical scavengers, moisturizers, depigmenting agents, liporegulators, anti-acne agents, antidandruff agents, anti-aging agents, softeners, antiwrinkle agents, keratolitic agents, anti-inflammatory agents, fresheners, healing agents, vascular protectors, antibacterial agents, antifungal agents, antiperspirants, deodorants, skin conditioners, anesthetics, immunomodulators, and nourishing agents, and the like.

The adhesive matrix may also include particles that are magnetic or magnetizable for improving microcirculation. The composite structure may include, for example, at least two layers of magnetizable particles capable of generating respective magnetic fields of different polarities.

The solvent may be a solvent other than water, for example, an oil or a lotion.

An exemplary treatment device in accordance with the invention may make it easy to package one or more active agents by incorporating them in one or more adhesive matrices. Storage may be performed in the anhydrous state under good conditions since it may be possible for the cover to be impregnated with solvent only at the time of use. This may make it possible to avoid using preservatives or to reduce the concentration thereof. Packaging may also be made simpler.

The mass per unit area of the matrix may range from 10 grams per square meter ($g/m^2$) to 100 $g/m^2$, for example.

In an exemplary embodiment, one of the layers in contact with the adhesive matrix may comprise a non-woven fabric. Optionally, the non-woven fabric may be laminated with a peel-off film, a net, a web, a woven cloth, a sponge, a felt, or the like. The adhesive matrix may be between two porous layers, each layer comprising, for example, a non-woven fabric.

The inside and outside faces of the cover may have different roughnesses. The layers between which the matrix is situated may have different thicknesses and/or pore sizes so as to make two different types of application possible, depending on which face is selected by the user, for example, by turning the cover inside out. The outside and inside faces of the cover may have different colors so as to make them easily identified by the user.

One surface of the cover, for example, the inside face, may comprise a heat-sealable web thereon. One of the two layers may comprise a non-woven fabric having two opposite surfaces, wherein the heat-sealable web may be on one of the surfaces of the non-woven fabric, and the other surface of the non-woven fabric may be bonded to the adhesive matrix. It should be understood that the web is not essential, it being possible for the sheet(s) constituting the cover to be assembled in numerous ways.

In an exemplary embodiment, the composite structure may include a layer that is impermeable or partially occlusive (i.e., semi-permeable) so as to encourage diffusion of an active agent into the skin by retarding evaporation of the solvent. This impermeable or partially occlusive layer may be between the matrix and the outside of the cover when the treatment is to take place inside the cover. In this configuration, the impermeable or partially occlusive layer may contribute to retaining the solvent inside the cover, which may be desired, for example, when the solvent is volatile or when only a small quantity of solvent is introduced into the cover.

The composite structure may also include at least two juxtaposed or superposed adhesive matrices of compositions. The compositions may be identical or different. For example, it may be desirable to assemble together two or more adhesive matrices in order to obtain a desired combination of active agents rather than attempt to incorporate all of the agents in a single adhesive matrix. For example, a given adhesive matrix may be manufactured in large quantity with one or more selected active agents. The matrix may then be assembled with one or more different adhesive matrices containing other active agents so as to build up a range of composite structures having a variety of properties.

According to an exemplary aspect of the invention, the composite structure may comprise, in order, the following superposition of layers: a first layer that is permeable to the solvent, a first adhesive matrix, a second adhesive matrix, and a second layer that is permeable to the solvent. According to another exemplary aspect, the composite structure may comprise, in order, the following superposition of layers: a first layer that is permeable to the solvent, a first adhesive matrix containing at least one active agent, an impermeable intermediate layer, a second adhesive matrix containing at least one active agent, and a second permeable layer. The first and second adhesive matrices may contain different active agents.

Such composite structures may be manufactured by coating each permeable layer separately in an adhesive matrix. The coated layers may then be assembled, either directly or otherwise, about an intermediate layer, for example, an impermeable layer or a permeable layer.

According to another exemplary aspect, the composite structure may include a first adhesive matrix comprising two juxtaposed regions containing different active agents. The composite structure may optionally comprise a second adhesive matrix likewise comprising two juxtaposed regions containing different active agents, for example, active agents that are different from those contained in the first adhesive matrix. This configuration may increase the number of combinations of active agents within a given composite structure and/or to adapt the distribution of the agent to the nature and the positioning of the zones to be treated.

The composite structure may also be arranged in such a manner as to encourage diffusion of one or more of the active agents contained in the adhesive matrix towards one of the faces of the cover. To create diffusion towards a face of the cover defined by a solvent-permeable layer, for example, a non-woven fabric, the adhesive matrix may be placed in the fluid state on the solvent-permeable layer so as to enable diffusion at least in part between the fibers or particles of the solvent-permeable layer, over at least a portion of the thickness thereof.

According to another exemplary aspect of the invention, a method of manufacturing a device for treating a part of the body is provided. The method may comprise providing at least one sheet comprising a composite structure of at least one adhesive matrix present between two layers, wherein at least one of the layers is permeable to a solvent. These two layers may be permanently bonded to the adhesive matrix. The adhesive matrix may contain at least one active agent soluble in the solvent and suitable, once dissolved, for being released through at least one side of the sheet. The method may also comprise folding the at least one sheet over onto itself or shaping it into a bag or assembling it with at least one other sheet, so as to create a cover defining a cavity in which a part of the body may be received.

According to another exemplary aspect, the composite structure can be made by coating a first layer with an adhesive matrix based on permanent adhesive, where the adhesive matrix contains at least one active agent and possibly a filler. The nature and the quantity of the active agent and/or the filler may be selected to enable the active agent to be released when the composite structure is wetted by a solvent. A second layer may be assembled with the coated first layer so that the adhesive matrix is sandwiched between the two layers. The layers may be bonded together permanently by the matrix, either directly or indirectly. At least one of the two layers may be permeable to a solvent capable of dissolving the active agent contained in the matrix. The second layer may be coated on one face in a second adhesive matrix, and the two adhesive matrices can then be stuck together. The two adhesive matrices may be united, even if they are identical in composition, so as to provide two different outer layers, for example, to obtain two faces offering specific application characteristics.

It should be appreciated that one or more exemplary aspects of the invention may make it easier to manufacture independently and in large quantities, for example, permeable layers each coated in an adhesive matrix containing one or more predetermined active agents. Subsequently, various combinations of active agents may be made by selecting which layers are to be assembled together depending on the use for which the treatment device is intended. For example, a composite structure may be made having two outside layers and two adhesive matrices containing active agents that need to be stored separately.

According to another exemplary aspect of the invention, various methods of treatment, such as cosmetic and/or dermatological treatment are provided. For example, a method of treating a part of the body may comprise inserting the part of the body to be treated inside the cavity defined by the cover of the treatment device and placing the cover in contact with a solvent. For example, the body part may be introduced before or after placing the cover in contact with the solvent.

Optionally, massaging motion may be imparted between the cover and the part of the body inserted therein. Such massaging may encourage the release of one or more of the active agents inside of the cover.

Optionally, after a first treatment, the cover may be turned inside-out and treatment may be started over using the inside-out cover.

An exemplary treatment method may also include selecting between two different faces of the cover prior to performing a first treatment.

A treatment device in accordance with one or more exemplary aspects of the invention may be used for any treatment in general. The treatment may be therapeutic. For example, the device may be used for treating diseases such as acne, cutaneous herpes, psoriasis, or the like.

In accordance with another exemplary aspect of the invention, a method of treating at least a portion of at least one hand may comprise inserting a hand into a glove comprising a cover as defined above and placing the cover in contact with solvent. For example, the hand may be inserted before or after placing the cover in contact with the solvent.

According to another exemplary aspect of the invention, a glove for treatment of at least a portion of at least one hand may include, for example, at least one moisturizing, anti-chapping, anti-herpes, burn-care, or eczema-care agent, or an agent that promotes healing.

Aside from the structural and procedural arrangement described above, the invention could include a number of other arrangements, such as those explained hereinafter. It is to be understood that both the foregoing description and the following description are exemplary and explanatory only and are not restrictive of the invention.

The accompanying drawings are included to provide a further understanding of the invention and are incorporated in and constitute a part of this specification. The drawings illustrate some exemplary embodiments of the invention and, together with the description, serve to explain some principles of the invention. In the drawings, FIG. 1 is a diagrammatic face view of a treatment glove made in accordance with the invention;

FIG. 2 is a diagrammatic cross-sectional view taken along line II-II of FIG. 1;

FIG. 3 is a side view of a glove finger embodiment in accordance with the invention;

FIG. 4 is a cross-sectional view taken along line IV-IV of FIG. 3;

FIG. 5 is a side view of alternative glove finger embodiment in accordance with the invention;

FIG. 6 is a cross-sectional view taken along line VI-VI of FIG. 5;

FIG. 7 shows a treatment cap embodiment in accordance with the invention;

FIG. 8 is a diagrammatic cross-sectional view taken along line VIII-VIII of FIG. 7;

FIG. 9 shows a treatment sock embodiment in accordance with the invention;

FIG. 10 shows a treatment bag embodiment in accordance with the invention;

FIG. 11 shows a treatment hood embodiment in accordance with the invention;

FIGS. 12 to 20 show various examples of structures that can be used;

FIG. 21 shows how the sheet example of FIG. 20 is manufactured;

FIG. 22 shows a variant embodiment of the FIG. 20 structure; and

FIG. 23 shows a detailed cross-sectional view of portion XXIII of FIG. 2.

Reference will now be made in detail to exemplary embodiments of the invention, examples of which are illustrated in the accompanying drawings. Wherever possible, the same reference numbers are used throughout the drawings and in the description to refer to the same or like parts.

In accordance with the invention, a closure system for a container is provided. Referring to FIG. 1 As shown in FIGS. 1 and 2, a treatment glove 10 may comprise two sheets 11 and 12 assembled together at the periphery in an assembly zone 13 (shown in dashed lines) to form a cover defining a cavity into which a hand can be inserted.

In the exemplary embodiment of FIGS. 1 and 2, the sheets 11 and 12 may be sufficiently flexible to enable the glove to be turned inside-out so as to make it capable of performing a new treatment, as described in greater detail below.

At least one of the two sheets 11 and 12 may include an adhesive matrix placed in permanent manner between at least two layers, optionally, in direct contact with the layers. The adhesive matrix may contain at least one active agent, and at least one of the layers may be permeable to a solvent such as, for example, water. The solvent may be capable of dissolving the active agent in order to cause it to be released while in contact with the surface to be treated.

The active agent may be released inside the cavity formed by the cover, outside the cavity, or both inside and outside, depending on the intended application.

The invention is not limited to a treatment device in the form of a glove. FIGS. 3-11 show other exemplary treatment devices, and the examples given are not limiting.

For example, FIG. 3 shows a finger glove 20 for treatment of a finger. The finger glove 20 comprises a tubular cover defining a cavity for receiving the finger. In the exemplary embodiment of FIGS. 3 and 4, the finger glove 20 may be formed by assembling two sheets 21 and 22 together along an assembly zone 23 (shown in dashed lines) at the periphery thereof.

FIGS. 5 and 6 show an exemplary finger glove 20' wherein the cavity may be formed using a single sheet 21' folded over onto itself and assembled together along an assembly zone 23' (shown in dashed lines). The assembly zone 23' may extend along one of the longitudinal edges of the sheet 21' and across the end remote from the finger-insertion opening.

FIGS. 7 and 8 show an exemplary treatment cap 30 formed by a sheet 31 shaped to form a bag. This sheet 31 is provided at its periphery with elastic 34 which may be held by a cuff 35. The elastic 34 may be assembled in the stretched state to the sheet 31 so that the sheet is gathered around its periphery when at rest. The treatment cap 30 may be used, for example, to apply care to the hair and/or to the scalp.

FIG. 9 shows an exemplary treatment sock 40 formed by assembling together two sheets 41 and 42 along their periphery in an assembly zone 43 (shown in dashed lines).

FIG. 10 shows an exemplary treatment bag 50 formed in similar manner to the treatment cap of FIG. 7 using a single sheet 51, but of smaller size, for example, a size suitable for containing an ear.

FIG. 11 shows an exemplary treatment hood 60 formed by assembling together two sheets 61 and 62 at their periphery along an assembly zone 63 (shown in dashed lines).

The exemplary treatment devices described above may include sheets comprising various composite structures. Some exemplary composite structures are described below.

For example, FIG. 12 shows a composite structure comprising an adhesive matrix II sandwiched between two layers I and III. At least one of the layers I and III may be permeable to a solvent, for example, water, an oil, or a lotion, for example, an alcohol-based lotion.

The adhesive matrix II may be based on a permanent adhesive which is not soluble in the solvent. The permanent adhesive may ensure that the two layers I and III remain together, even when the composite structure is wetted. The adhesive matrix II may contain, for example, at least one water-soluble active agent for cleaning, making up, or caring for the skin or the hair, and a filler enabling it to release at least one of the active agents it contains when the composite structure is impregnated in solvent. The adhesive matrix II may be based on vinyl compounds, polyvinyl alcohol (PVA), polyvinyl pyrrolidone (PVP), a pseudo-latex such as acrylic polymers, polyurethane, latex elastomer, or the like. The selected adhesive may be reversible, for example, PVA and PVP, or not reversible, for example, acrylics, vinyl compounds, polyurethanes, and latex elastomers.

When the solvent is water, the adhesive matrix II may contain a filler capable of enabling it to absorb water so that it loses its cohesion and so that the water-soluble active agents it contains may be released more easily when the composite structure is wetted. The filler may comprise particles of a water-absorbing material, such as a polyacrylate, for example.

In general, it is possible to incorporate 0.01% to 50% active agents in the adhesive matrix II, for example, agents selected from vitamin C, vitamin A, vitamin F, laponite, glycerin, wetting agents, collagen, salicylic acid, essential aromatic oils, coloring agents, and caffeine. It may also be possible to incorporate in the adhesive matrix a powder filler of an inert material, for example, ORGASOL.

Layers I and III may comprise various permeable flexible components that are optionally extensible, such as, for example, a textile film, a non-woven fabric, a cellular material such as a foam, a felt, or any laminated material including one of the above components laminated with one or more other components selected from the above components. One of the layers I and III can also include one or more flexible components that are impermeable or possibly occlusive, for example, a plastics film, optionally metal-coated, or a sheet of metal. The layers I and III may, by the nature of the materials from which they are made, be intrinsically hydrophilic or hydrophobic and may be subjected to treatment for making them hydrophilic or hydrophobic. The layers I and III may have different thicknesses, different natures, different colors, different roughnesses, or the like.

At least one of the layers I and III may have perforations 100 (e.g., slots) as shown in FIGS. 13 and 14. These perforations 100 (e.g., slots) may encourage the active agents contained in the adhesive matrix to diffuse towards the skin, and they can open to the outside or to the inside of the cover. It should be observed that the perforations 100 may be sufficiently narrow to prevent the adhesive matrix from coming directly into contact with the skin. The perforations 100 may contribute to making the cover stretchable.

At least one of the layers I and III may be coated in flocking 105, as shown in FIG. 15.

The composite structure may comprise an adhesive matrix II sandwiched between layers I and III of different thicknesses, as shown in FIG. 16. The outer layers I and III may comprise, for example, non-woven fabrics having different textures, for example, one being softer and the other being rougher. The user can thus choose at the time of use between two types of surface, for example, depending on whether impurities are to be cleansed from the surface of the skin or whether ordinary surface cleaning is to be performed. The particular surface selected may be used by turning the cover inside-out, if desired.

One of the layers I and III of the sheet may have a surface web 110 to make it easier to assemble with another sheet, for example, by heat-sealing, as shown in FIG. 17. The web 110 may be laminated on a non-woven fabric, for example.

In order to encourage active agents to diffuse towards one face of the cover, the matrix may impregnate one of the layers I and III through at least a fraction of its thickness, as shown in FIG. 18. This may be achieved, for example, by depositing the matrix in the fluid state on one of the layers I and III, so as to enable it to diffuse into the layer.

A plurality of adhesive matrices may be superposed directly or indirectly, thus making it possible to create a wide variety of combinations of active agents and/or support layers having different properties. The adhesive matrices be assembled together in various ways, for example they can be stuck together or they can be individually sandwiched between layers that are permeable or impermeable.

For example, FIG. 19 shows a composite structure comprising a subassembly II sandwiched between two outer layers I and III. The subassembly II may comprise two adhesive matrices IIa and IIb placed on opposite sides of an intermediate layer 115. The adhesive matrices IIa and IIb may contain, for example, different active agents. Consequently, the user may treat the skin in different ways, depending on whether the adhesive matrix IIa is situated towards the outside or towards the inside of the cover.

The intermediate layer 115 may be impermeable, in which case the active agents contained in the matrix IIb will not diffuse towards the matrix IIb, and vice versa. Alternatively, the intermediate layer 115 may be permeable.

FIG. 20 shows a composite structure having an adhesive matrix II comprising two sub-matrices IIa and IIb stuck together and sandwiched between layers I and III. One of the layers I and III may be occlusive and situated on the inside or on the outside of the cover.

For example, the adhesive matrices IIa and IIb may contain different active agents, for example, active agents unsuitable for being packaged together.

In order to make the composite structure shown in FIG. 20, it may be possible, as shown in FIG. 21, to begin with layers I and III, which are coated in conventional coating stations 120 and 130 with the adhesive matrices IIa and IIb. These matrices may contain solvents during manufacture so as to make the coating operation easier. These solvents may be volatile and may be eliminated from the final composite structure. The coated layers I and III may then be stuck together to form the final composite structure.

It should be appreciated that a plurality of layers may be made independently, wherein each layer may be impregnated with an adhesive matrix containing predetermined active agents. Subsequently, the coated layers may be assembled so as to obtain a desired combination of active agents.

FIG. 22 shows an adhesive matrix comprising a plurality of regions IIc, IId, IIe, and IIf containing different active agents. This configuration may be used, for example, when it may be desired to package a plurality of active agents in a single adhesive matrix even though the agents may need to be stored separately. The configuration of FIG. 22 may also be used for multiplying the number of active agents that are stored separately in a single sheet.

For example, the region IIc may contain vitamin C, the region IId may contain an enzyme, the region IIe may contain bicarbonate, and the region IIf may contain citric acid. After the cover has been put into contact with a solvent such as water, these various compounds may be released and may form foaming retinol for treating signs of aging.

For example, a treatment glove as in FIG. 1 may comprise the structure shown in FIG. 23. The layer III situated on the inside of the glove may comprise, for example, a non-woven polyethylene fabric laminated with a heat-sealable web. The adhesive matrix II may be based on a permanent polyacrylic adhesive containing glycerin. The outer layer I may comprise, for example, a non-woven fabric. In use, a hand may be inserted into the glove and then water may be poured inside the glove. The hand may be clenched several times. After the hand has been extracted from the glove, it may be allowed to dry. The hand may not be greasy and, for a period of several hours, the hand may feel less damp than a hand that has not been treated.

The invention is not limited to the examples described above. For example, other combinations of layers and adhesive matrices can be used.

The adhesive matrix may also be used as a supply of active agents with the composite structure being wetted several times over.

It may be possible to use a solvent other than water for wetting the composite structure, and said solvent may be compatible with external use on the user.

It will be apparent to those skilled in the art that various modifications and variations can be made to the structure and methodology of the present invention. Thus, it should be understood that the invention is not limited to the examples discussed in the specification. Rather, the present invention is intended to cover modifications and variations.

What is claimed is:

1. A treatment device, comprising:
   a cover defining a cavity, the cavity being configured to receive a part of a body, the cover comprising
   at least one sheet having a composite structure, the composite structure comprising
      at least two layers, at least one of the two layers being permeable to a solvent, and
      at least one adhesive matrix situated between the two layers, the two layers being permanently bonded to the adhesive matrix, the adhesive matrix containing at least one active agent that is soluble in the solvent,
   wherein, when the active agent is dissolved in the solvent, the active agent is released from at least one side of the cover, and
   wherein the device is configured so that the active agent is released into the cavity.

2. A device according to claim 1, wherein the cover is configured as a glove.

3. A device according to claim 1, wherein the cover is configured as one of a cap, a finger glove, a hood, a sock, and a bag configured to cover an ear.

4. A device according to claim 1, wherein the cover is elasticized.

5. A device according to claim 1, wherein the cover comprises a single sheet folded onto itself.

6. A device according to claim 1, wherein the cover comprises a single sheet shaped to form a bag.

7. A device according to claim 1, wherein the cover comprises a plurality of sheets attached together.

8. A device according to claim 7, wherein the plurality of sheets are attached along a portion of a periphery of the device.

9. A device according to claim 7, wherein the sheets are attached by one of heat-sealing, an adhesive, and stitching.

10. A device according to claim 1, wherein the adhesive matrix contains at least one additional active agent configured to swell when contacted by the solvent, the adhesive matrix containing a sufficient quantity of the at least one additional active agent such that the adhesive matrix loses cohesion on contact with the solvent and releases the active agent more easily.

11. A device according to claim 1, wherein the adhesive matrix contains at least one additional active agent soluble in the solvent, the adhesive matrix containing a sufficient quantity of the at least one additional active agent such that the adhesive matrix loses cohesion on contact with the solvent and releases the active agent more easily.

12. A device according to claim 1, wherein the adhesive matrix contains at least one additional active agent soluble in the solvent and configured to swell when contacted by the solvent, the adhesive matrix containing a sufficient quantity of the at least one additional active agent such that the adhesive matrix loses cohesion on contact with the solvent and releases the active agent more easily.

13. A device according to claim 1, wherein the at least one active agent is configured to swell when contacted by the solvent, the adhesive matrix containing a sufficient quantity of the at least one additional active agent such that the adhesive matrix loses cohesion on contact with the solvent and releases the active agent more easily.

14. A device according to claim 1, wherein the adhesive matrix contains a filler comprising at least one compound configured to swell on contact with the solvent, the adhesive matrix containing a sufficient quantity of the at least one compound such that the matrix loses its cohesion on contact with the solvent and releases the active agents more easily.

15. A device according to claim 1, wherein the adhesive matrix contains a filler comprising at least one substantially inert compound, the adhesive matrix containing a sufficient quantity of the at least one compound such that the matrix loses its cohesion on contact with the solvent and releases the active agents more easily.

16. A device according to claim 1, wherein the solvent comprises water.

17. A device according to claim 1, wherein the solvent comprises an oil.

18. A device according to claim 1, wherein the solvent comprises a lotion.

19. A device according to claim 1, wherein the adhesive matrix contains at least one moisture-absorbing compound.

20. A device according to claim 19, wherein the adhesive matrix contains 0.2% to 60% by weight of the at least one moisture-absorbing compound.

21. A device according to claim 20, wherein the adhesive matrix contains 0.5% to 40% by weight of the at least one moisture-absorbing compound.

22. A device according to claim 19, wherein the at least one moisture-absorbing compound is chosen from polyacrylates, silicas, cotton fibers, starches, alginates, calcium carbonate, magnesium carbonate, viscose, cellulose, and lyophylisates.

23. A device according to claim 1, wherein the adhesive matrix contains at least one substance configured to lower adhesive strength of the adhesive matrix and to enable the adhesive matrix to burst when contacted by the solvent so as to facilitate release of the active agents.

24. A device according to claim 23, wherein the at least one substance is substantially inert.

25. A device according to claim 24, wherein the at least one substance comprises at least one of microbeads of an inert compound and powder of an inert compound.

26. A device according to claim 25, wherein the powder of an inert compound comprises a polyamide powder.

27. A device according to claim 1, wherein the active agent is chosen from vitamin C, vitamin A, vitamin F, glycerin, laponite, wetting agents, collagen, salicylic acid, tio acid, essential aromatic oils, coloring agents, caffeine, anti-oxidants, free radical scavengers, moisturizers, depigmenting agents, liporegulators, anti-acne agents, antidandruff agents, anti-aging agents, softeners, antiwrinkle agents, keratolitic agents, anti-inflammatory agents, fresheners, healing agents, vascular protectors, antibacterial agents, antifungal agents, antiperspirants, deodorants, skin conditioners, anesthetics, immunomodulators, and nourishing agents.

28. A device according to claim 1, wherein the adhesive matrix contains at least one of magnetic particles and magnetizable particles.

29. A device according to claim 1, wherein at least one of the two layers comprises a non-woven fabric.

30. A device according to claim 1, wherein each of the two layers comprises a non-woven fabric.

31. A device according to claim 1, wherein the cover comprises an inside surface and an outside surface, the inside surface having a different roughness than the outside surface.

32. A device according to claim 1, wherein each of the two layers has a porosity differing from one another.

33. A device according to claim 1, wherein each of the two layers has a color differing from one another.

34. A device according to claim 1, wherein each of the two layers has a thickness differing from one another.

35. A device according to claim 1, wherein the cover has a surface comprising a heat-sealable web thereon.

36. A device according to claim 35, wherein one of the two layers comprises a non-woven fabric having two opposite surfaces, wherein the heat-sealable web is on one of the surfaces of the non-woven fabric and the other surface of the non-woven fabric is bonded to the adhesive matrix.

37. A device according to claim 1, wherein at least one of the two layers is at least partially impermeable.

38. A device according to claim 37, wherein the at least partially impermeable layer is between the adhesive matrix and an outside of the cover.

39. A device according to claim 1, wherein the composite structure comprises at least two adhesive matrices of identical compositions, the at least two adhesive matrices being one of juxtaposed and superposed.

40. A device according to claim 1, wherein the composite structure comprises at least two adhesive matrices of at least two different compositions, the at least two adhesive matrices being one of juxtaposed and superposed.

41. A device according to claim 1, wherein the composite structure comprises a superposition of layers comprising, in order, a first solvent-permeable layer, a first adhesive matrix, a second adhesive matrix, and a second solvent-permeable layer.

42. A device according to claim 1, wherein the composite structure comprises a superposition of layers comprising, in order, a first permeable layer, a first adhesive matrix containing at least one active agent, an impermeable intermediate layer, a second adhesive matrix containing at least one active agent, and a second permeable layer, the first and second adhesive matrices containing different active agents.

43. A device according to claim 1, wherein the at least one sheet is configured to enable the active agent to diffuse towards one side of the cover.

44. A device according to claim 43, wherein the at least one sheet is configured to enable the active agent to diffuse towards the inside of the cover.

45. A method of manufacturing a device for treating a part of the body, the method comprising: providing at least one sheet comprising a composite structure of at least one adhesive matrix between at least two layers, at least one of the two layers being permeable to a solvent, the two layers being permanently bonded to the adhesive matrix, the adhesive matrix containing at least one active agent soluble in the solvent, the at least one active agent being released through at least one side of the sheet when dissolved; and
at least one of folding the at least one sheet over onto itself, shaping the at least one sheet into a bag, and assembling the at least one sheet with at least one other sheet, so as to form a cover defining a cavity in which a part of a body may be received.

46. A method of treating a part of the body, the method comprising: introducing a body part to be treated into the cavity defined by the cover of the treatment device of claim 1; and
placing the cover in contact with a solvent.

47. A method according to claim 46, further comprising imparting massaging movement between the cover and the part of the body in the cavity.

48. A method according to claim 46, further comprising, after a first treatment, turning the cover inside-out and repeating treatment using the inside-out cover.

49. A method according to claim 46, wherein the cover is placed in contact with the solvent before introducing the body part into the cavity.

50. A method according to claim 46, wherein the cover is placed in contact with the solvent after introducing the body part into the cavity.

51. A glove for treating at least a portion of at least one hand, the glove comprising the device of claim 1.

52. A glove according to claim 51, including at least one of a moisturizing, anti-chapping, anti-herpes, burn-care, eczema-care, and healing-promoting agent.

53. A method of treating at least a portion of at least one hand, the method comprising:
inserting a hand into the glove of claim 51; and
placing the glove in contact with a solvent.

54. A method according to claim 53, wherein the cover is placed in contact with the solvent before introducing the body part into the cavity.

55. A method according to claim 53, wherein the cover is placed in contact with the solvent after introducing the body part into the cavity.

56. A device according to claim 31, wherein the inside source is a surface of the non-woven fabric.

57. A device according to claim 1, wherein the non-woven layer is permeable to a solvent.

58. A device according to claim 1, wherein the device is configured to treat an exterior body surface with the active agent.

59. A device according to claim 1, wherein the device is configured to treat the part of a body received in the cavity.

60. A treatment device, comprising:
a cover defining a cavity, the cavity being configured to receive a body part of a body, the cover comprising
at least one sheet having a composite structure, the composite structure comprising
at least two layers, at least one of the two layers being permeable to a solvent, wherein at least one of the two layers is at least partially impermeable, and at least one adhesive matrix situated between the two layers, the two layers being permanently bonded to the adhesive matrix, the adhesive matrix containing at least one active agent that is soluble in the solvent, wherein, when the active agent is dissolved in the solvent, the active agent is release from at least one side of the cover, and wherein the adhesive matrix is between the at least partially impermeable layer and the cavity.

61. A treatment device, comprising:

a cover defining a cavity, the cavity being configured to receive a part of a body, the cover comprising at least one sheet having a composite structure, the composite structure comprising a first layer and a second layer, the first layer and second layer being permeable to a solvent, and a first adhesive matrix situated between the first layer and the second layer, the first layer being permanently bonded to the first adhesive matrix, the first adhesive matrix containing at least a first active agent that is soluble in the solvent, a second adhesive matrix situated between the first layer and the second layer, the second adhesive layer being permanently bonded to the first adhesive matrix and the second layer, the second adhesive matrix containing at least a second active agent that is soluble in the solvent, wherein the cover is configured such that when the first active agent is dissolved in the solvent, the first active agent is released through the first layer and, when the second active agent is dissolved in the solvent, the second active agent is released through the second layer.

62. A treatment device, comprising:

a cover defining a cavity, the cavity being configured to receive a part of a body, the cover comprising at least one sheet having a composite structure, the composite structure comprising at least two layers, at least one of the two layers being permeable to a solvent, wherein at least one of the two layers comprising a non-woven fabric, and at least one adhesive matrix situated between the two layers, the two layers being permanently bonded to the adhesive matrix, the adhesive matrix containing at least one active agent that is soluble in the solvent, wherein, when the active agent is dissolved in the solvent, the active agent is released from at least one side of the cover.

63. A treatment device, comprising:

a cover defining a cavity, the cavity being configured to receive a part of a body, the cover comprising at least one sheet having a composite structure, the composite structure comprising at least two layers, at least one of the two layers being permeable to a solvent, and at least one adhesive matrix situated between the two layers, the two layers being permanently bonded to the adhesive matrix, the adhesive matrix containing at least one active agent that is soluble in the solvent, wherein, when the active agent is dissolved in the solvent, the active agent is released from at least one side of the cover, and wherein the device is configured to treat an exterior body surface with the active agent.

\* \* \* \* \*